United States Patent
Mikami

(10) Patent No.: US 11,030,745 B2
(45) Date of Patent: Jun. 8, 2021

(54) IMAGE PROCESSING APPARATUS FOR ENDOSCOPE AND ENDOSCOPE SYSTEM

(71) Applicant: OLYMPUS CORPORATION, Hachioji (JP)

(72) Inventor: Toshiaki Mikami, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 1 day.

(21) Appl. No.: 16/684,536

(22) Filed: Nov. 14, 2019

(65) Prior Publication Data

US 2020/0082529 A1 Mar. 12, 2020

Related U.S. Application Data

(63) Continuation of application No. PCT/JP2017/018362, filed on May 16, 2017.

(51) Int. Cl.
*H04N 13/324* (2018.01)
*H04N 13/239* (2018.01)
(Continued)

(52) U.S. Cl.
CPC .......... *G06T 7/0012* (2013.01); *G06K 9/4652* (2013.01); *G06T 7/20* (2013.01); *G06T 7/593* (2017.01); *G06T 7/70* (2017.01); *H04N 13/239* (2018.05); *H04N 13/324* (2018.05); *H04N 13/361* (2018.05); *A61B 1/00009* (2013.01); *A61B 1/00193* (2013.01); *A61B 1/04* (2013.01);
(Continued)

(58) Field of Classification Search
None
See application file for complete search history.

(56) References Cited

U.S. PATENT DOCUMENTS

2016/0004144 A1* 1/2016 Laroia ................. H04N 5/2258
348/222.1
2017/0265946 A1* 9/2017 Ramachandran .. A61B 1/00013

FOREIGN PATENT DOCUMENTS

JP 2013074397 A 4/2013
JP 2013183313 A * 9/2013
(Continued)

OTHER PUBLICATIONS

International Preliminary Report on Patentability (IPRP) dated Nov. 28, 2019 (and English translation thereof), issued in International Application No. PCT/JP2017/018362.
(Continued)

*Primary Examiner* — Edemio Navas, Jr.
(74) *Attorney, Agent, or Firm* — Holtz, Holtz & Volek PC

(57) ABSTRACT

An image processing apparatus for an endoscope includes processing circuitry. The processing circuitry acquires a left image and right image. The processing circuitry generates a three-dimensional display image based on the left image and right image. The processing circuitry sets a first region in a part of the left image or right image. The first region is a region having a blur. The processing circuitry sets a second region in the left image or right image. The second region is a region where the user is performing treatment. The processing circuitry computes an overlapping region between the first region and the second region. The processing circuitry determines whether or not to notify the user based on the overlapping region. The processing circuitry generates information for notifying.

14 Claims, 16 Drawing Sheets

(51) Int. Cl.
*H04N 13/361* (2018.01)
*G06T 7/593* (2017.01)
*G06T 7/00* (2017.01)
*G06T 7/20* (2017.01)
*G06T 7/70* (2017.01)
*G06K 9/46* (2006.01)
*A61B 1/00* (2006.01)
*A61B 1/04* (2006.01)

(52) U.S. Cl.
CPC .................. *G06K 2209/057* (2013.01); *G06T 2207/10012* (2013.01); *G06T 2207/10024* (2013.01); *G06T 2207/10068* (2013.01); *G06T 2207/30168* (2013.01)

(56) References Cited

FOREIGN PATENT DOCUMENTS

| | | |
|---|---|---|
| JP | 2013183313 A | 9/2013 |
| JP | 2016170182 A | 9/2016 |

OTHER PUBLICATIONS

International Search Report (ISR) dated Aug. 15, 2017 (and English translation thereof), issued in International Application No. PCT/JP2017/018362.

Written Opinion of the International Searching Authority dated Aug. 15, 2017 issued in International Application No. PCT/JP2017/018362.

* cited by examiner

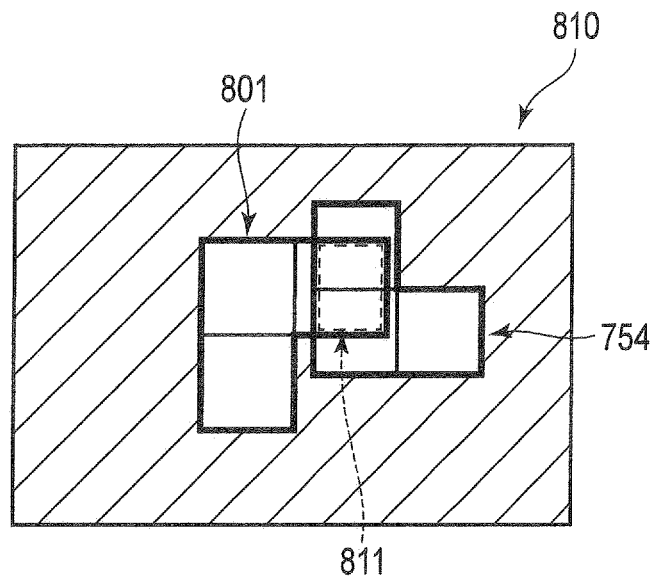
F I G. 16
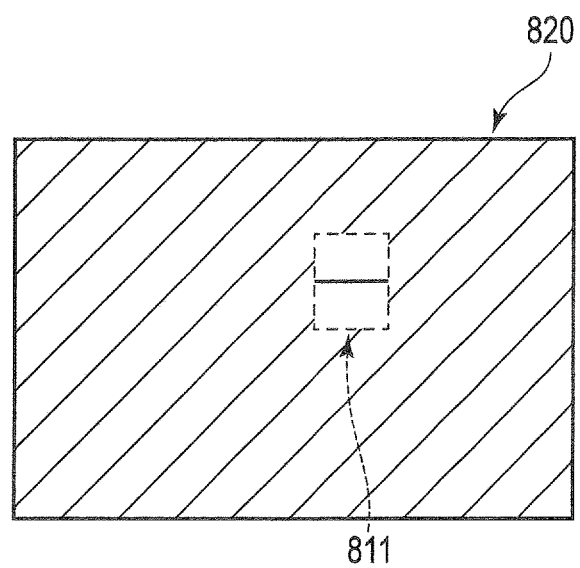
F I G. 17

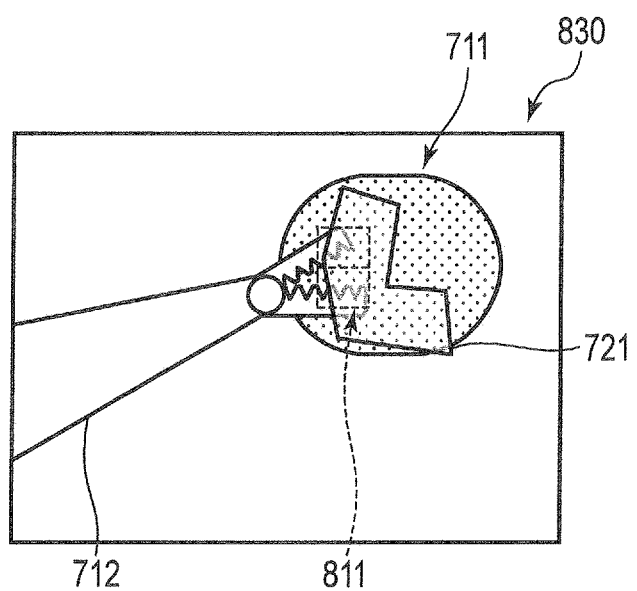
F I G. 18

US 11,030,745 B2

IMAGE PROCESSING APPARATUS FOR ENDOSCOPE AND ENDOSCOPE SYSTEM

CROSS-REFERENCE TO RELATED APPLICATIONS

This application is a Continuation Application of PCT Application No. PCT/JP2017/018362, filed May 16, 2017, the entire contents of which are incorporated herein by reference.

FIELD

The embodiments relate to an image processing apparatus for an endoscope and an endoscope system.

BACKGROUND

In recent years, a three-dimensional endoscope using stereoscopic vision with parallax left and right images may be used. A stereo camera such as a three-dimensional endoscope generally includes two optical systems, and captures an image with parallax from the left and right optical systems to thereby obtain a stereoscopically visible subject image. With regard to such a stereo camera, when dirt adheres to one of the left and right optical systems, for example, only an image seen by one of the eyes is deteriorated, causing inconsistency between the left and right images and giving the user a sense of discomfort. Hereinafter, a state in which only an image seen by one of the eyes is deteriorated is referred to as "one-eye blurring". However, since humans perceive high-frequency images preferentially, it is difficult for a user to recognize the one-eye blurring that causes a sense of discomfort. Therefore, the user observes an image causing a sense of discomfort for a long time, leading to fatigue.

Regarding an imaging system having a stereo camera, Jpn. Pat. Appln. KOKAI Publication No. 2013-74397, for example, discloses a technology for detecting a state in which one of two images with different viewpoints is deteriorated and displaying a warning that the lens on one side is dirty. With this technology, frequency components in entire left and right images or frequency components in divided regions of the left and right images are computed. When the computed frequency components of the two images have a difference of a certain level or more, it is determined that one of the images is deteriorated, and when it is determined several times that one of the images is deteriorated, a warning indicating that the lens is dirty is displayed.

SUMMARY

An image processing apparatus for an endoscope includes processing circuitry. The processing circuitry acquires a pair of a left image and right image. The processing circuitry generates a three-dimensional display image for three-dimensional observation by a user based on the pair of the left image and right image. The processing circuitry sets a first region in a part of one of the left image or right image. The first region is a region having a blur. The processing circuitry sets a second region in the left image or right image. The second region is a region where the user is performing treatment. The processing circuitry computes an overlapping region between the first region and the second region. The processing circuitry determines whether or not to notify the user based on presence or absence of the overlapping region. The processing circuitry generates information for notifying the user that the second region has a blur, when the user is to be notified and the user performs three-dimensional observation.

Advantages of the embodiments will be set forth in the description which follows, and in part will be obvious from the description, or may be learned. The advantages may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments, and together with the general description given above and the detailed description of the embodiments given below, serve to explain the principles.

FIG. 16 is a schematic diagram for explaining computation of an uncomfortable region according to the first embodiment.

FIG. 17 is a schematic diagram showing an example of uncomfortable-region information according to the first embodiment.

FIG. 18 is a schematic diagram showing an example of a notification image according to the first embodiment.

DETAILED DESCRIPTION

First Embodiment

A first embodiment will be described. The present embodiment relates to a three-dimensional (3D) endoscope system. The endoscope system according to the present embodiment is configured so that, when a three-dimensionally displayed image is in a condition that may give a user a sense of discomfort when three-dimensionally observed, the user is notified that he or she may feel a sense of discomfort if he or she continues to use the endoscope system.

A 3D endoscope includes a stereo camera including a pair of left and right optical systems and an imaging element, and captures a pair of left and right subject images. A left (left-eye) image captured by the left (left-eye) optical system and a left (left-eye) imaging element, and a right (right-eye) image captured by the right (right-eye) optical system and a right (right-eye) imaging element are both obtained as subject images with parallax, similar to images viewed by a human with eyes. The endoscope system causes the user to perceive a stereoscopic image of the subject by displaying an image based on the left image and the right image on a three-dimensional display device.

<Configuration of Endoscope System>

Figure 1:
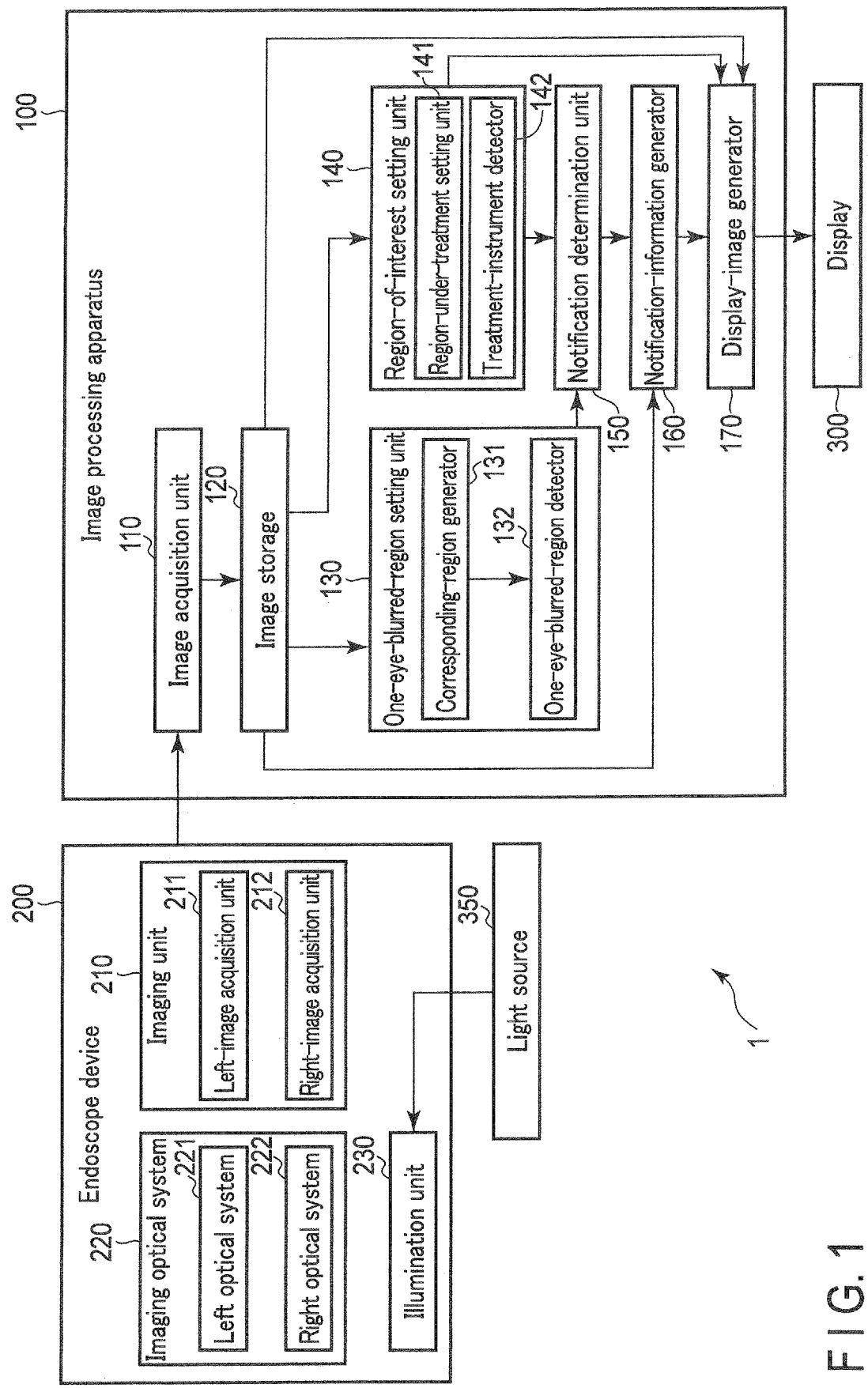
FIG. 1 is a block diagram showing an outline of a configuration example of an endoscope system according to a first embodiment.

An outline of a configuration example of an endoscope system 1 according to the present embodiment is shown in the form of a block diagram in FIG. 1, to describe a configuration of the endoscope system 1 with reference to FIG. 1. The endoscope system 1 includes an image processing apparatus 100, an endoscope device 200, a display 300, and a light source 350. The endoscope device 200 images the inside of a subject by inserting a part of the endoscope device into the subject, and generates image data of the inside of the subject. The image processing apparatus 100 acquires the image data generated by the endoscope device 200, and performs various kinds of image processing, etc., on the image data. The display 300 displays the image processed by the image processing apparatus 100. The light source 350 is a light source of illumination light for illuminating a range to be imaged by the endoscope device 200.

The endoscope device 200 is, for example, a surgical rigid scope, and has an elongated insertion portion configured to be inserted into a subject. The endoscope device 200 is connected with the image processing apparatus 100 and the light source 350 via a cable or the like. For example, a distal end of the insertion portion is provided with a bending portion that actively bends, and the bending portion may be configured to bend the distal end in a direction desired by the user according to the user's operation.

An imaging unit 210, an imaging optical system 220, and an illumination unit 230 are provided at the distal end of the insertion portion. The imaging unit 210 and the imaging optical system 220 have left and right optical systems in order to acquire a 3D image. The imaging unit 210 includes a left-image acquisition unit 211 and a right-image acquisition unit 212 each including an imaging element such as a CCD image sensor. The imaging optical system 220 includes a left optical system 221 that forms a subject image so as to focus on an imaging surface of the imaging element of the left-image acquisition unit 211, and a right optical system 222 that forms a subject image so as to focus on an imaging surface of the imaging element of the right-image acquisition unit 212. The illumination unit 230 includes an optical system that emits, in a direction of the subject, illumination light emitted from the light source 350 and guided by an optical fiber.

The image of the subject illuminated by the illumination light emitted from the illumination unit 230 is focused on the imaging surface of the imaging element of the imaging unit 210 via the imaging optical system 220. The imaging unit 210 generates image data (subject image) based on a subject image through an imaging operation. The subject image includes a left image generated by the left-image acquisition unit 211 and a right image generated by the right-image acquisition unit 212. The subject image is transmitted to the image processing apparatus 100 via a cable.

The image processing apparatus 100 includes an image acquisition unit 110, an image storage 120, a one-eye-blurred-region setting unit 130, a region-of-interest setting unit 140, a notification determination unit 150, a notification-information generator 160, and a display-image generator 170.

The image acquisition unit 110 acquires a subject image from the endoscope device 200. The image storage 120 separately stores the left image and the right image of the subject image acquired by the image acquisition unit 110. The image storage 120 includes, for example, a semiconductor memory such as a DRAM. In the image processing apparatus 100, various kinds of processing are performed using the images stored in the image storage 120. The image storage 120 according to the present embodiment holds a current subject image and a subject image of at least one frame before, that is, a past subject image, as images used for various kinds of processing.

Figure 2A:
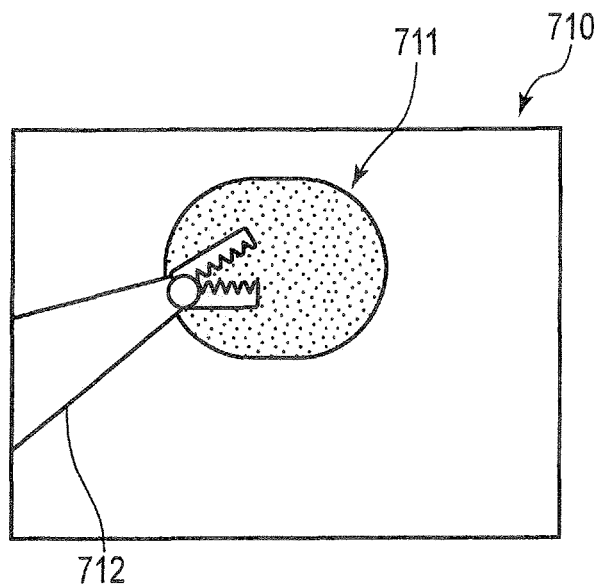
FIG. 2A is a schematic diagram showing an example of a left image acquired by an endoscope device according to the first embodiment, in order to illustrate a one-eye-blurred region.
Figure 2B:
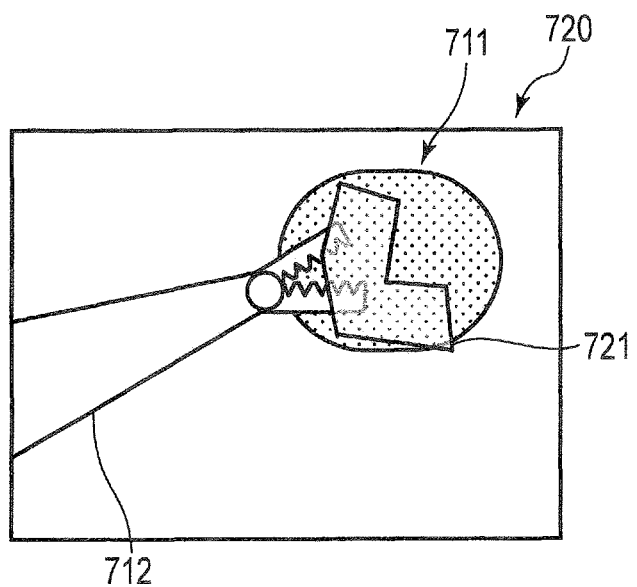
FIG. 2B is a schematic diagram showing an example of a right image acquired by the endoscope device according to the first embodiment, in order to illustrate a one-eye-blurred region.

The one-eye-blurred-region setting unit 130 acquires the left image and the right image from the image storage 120. The one-eye-blurred-region setting unit 130 sets a one-eye-blurred region by comparing the left image and the right image. The one-eye-blurred region (or a first region) will be described by taking as an example a case where a left image 710 (as shown in FIG. 2A) and a right image 720 (as shown in FIG. 2B) are acquired by the endoscope device 200 as a subject image. In the left image 710 shown in FIG. 2A and the right image 720 shown in FIG. 2B, an organ 711, which is a living body to be treated, and forceps 712 as a treatment instrument are shown. On the other hand, among the left image 710 and the right image 720, only the right image 720 includes a region 721 with reduced visibility near a distal end of the forceps 712 (the organ 711 under treatment). In the present embodiment, the state in which only one of the left image and the right image acquired simultaneously includes a region with reduced visibility, as described above, is defined as "one-eye blurring". The region 721 can also be expressed as a region in which the image is not clear, or as a region where a contrast value is low as compared to other regions. The one-eye blurring may be caused when only one of the left and right imaging optical systems 220 is contaminated by, for example, adhesion of water, oil, a tissue fragment, etc., in the living body and an image taken by the optical system is distorted, as compared to an original image, due to the influence of an attached substance. The one-eye-blurred-region setting unit 130 according to the present embodiment compares the acquired left image 710 and right image 720, as described above, and sets the region that is blurred only in one of the left image or the right image as a one-eye-blurred region.

The one-eye-blurred-region setting unit 130 includes a corresponding-region generator 131 and a one-eye-blurred-region detector 132. The corresponding-region generator 131 sets corresponding regions based on the corresponding points of the left image and the right image. The one-eye-blurred-region detector 132 detects the one-eye-blurred region based on the difference between the contrast values of the corresponding regions of the left image and the right image. The one-eye-blurred-region setting unit 130 outputs information related to the one-eye-blurred region (one-eye-blurred-region information) to the notification determination unit 150.

The region-of-interest setting unit 140 acquires the left image and the right image from the image storage 120. The region-of-interest setting unit 140 includes at least a region-under-treatment setting unit 141. The region-under-treatment setting unit 141 includes a treatment-instrument detector 142 that acquires, as a treatment-instrument region (or a fourth region) for each of the left image and the right image, a region where a treatment instrument with which treatment is being performed is present. The treatment-instrument detector 142 detects a treatment-instrument region in the pair of left and right images that indicates a treatment instrument used by the user through, for example, the use of color information. The region-under-treatment setting unit 141 sets a region with a high degree of being at a distal end in the treatment-instrument region, at least as a region under treatment (or a third region). Details of the degree of being at a distal end will be described later. The region-of-interest setting unit 140 sets at least a region under treatment as a region of interest (or a second region). The region-of-interest setting unit 140 outputs information related to the region of interest (region-of-interest information) to the notification determination unit 150 and the display-image generator 170.

The notification determination unit 150 acquires the one-eye-blurred-region information from the one-eye-blurred-region setting unit 130, and acquires the region-of-interest information from the region-of-interest setting unit 140. The notification determination unit 150 sets an uncomfortable region based on the one-eye-blurred-region information and the region-of-interest information. The notification determination unit 150 determines whether or not an image (3D image) causes a sense of discomfort (determination of a sense of discomfort) based on the presence or absence of the uncomfortable region. The notification determination unit 150 outputs the result of the determination of the sense of discomfort to the notification-information generator 160.

The notification-information generator 160 acquires the left image and the right image from the image storage 120. Also, the notification-information generator 160 acquires, from the notification determination unit 150, information related to the uncomfortable region (uncomfortable-region information) and the result of the determination of the sense of discomfort. The notification-information generator 160 changes a signal value of image information of the uncomfortable region for either one or both of the left image and the right image. After changing the signal value of the image information of the uncomfortable region, the notification-information generator 160 reduces the image to generate an uncomfortable-region image. The notification-information generator 160 outputs an uncomfortable-region image to the display-image generator 170.

The display-image generator 170 (three-dimensional image generator) acquires the left image and the right image from the image storage 120. The display-image generator 170 acquires the region-of-interest information from the region-of-interest setting unit 140, and acquires the uncomfortable-region image from the notification-information generator 160. The display-image generator 170 performs the other form of image processing on the image corrected by the notification-information generator 160. The image processing includes various kinds of processing for forming an image (display image) suitable for display on the display 300, and also includes, for example, image processing for displaying a three-dimensional image. Also, when generating the display image, the display-image generator 170 superimposes the uncomfortable-region image on an end portion farthest from the region of interest for each of the left image and the right image. The display-image generator 170 outputs the display image (three-dimensional display image) to the display device (display 300).

The one-eye-blurred-region setting unit 130, the region-of-interest setting unit 140, the notification determination unit 150, the notification-information generator 160, the display-image generator 170, etc., include, for example, an integrated circuit such as an application specific integrated circuit (ASIC), a field programmable gate array (FPGA), a graphics processing unit (GPU), or a central processing unit (CPU). The one-eye-blurred-region setting unit 130, the region-of-interest setting unit 140, the notification determination unit 150, the notification-information generator 160, the display-image generator 170, etc., may each be configured by a single integrated circuit or the like, or by a combination of a plurality of integrated circuits. Also, two or more of the one-eye-blurred-region setting unit 130, the region-of-interest setting unit 140, the notification determination unit 150, the notification-information generator 160, the display-image generator 170, and the like may be configured by a single integrated circuit or the like. The operation of these integrated circuits is performed in accordance with a program stored in a storage device provided in the image processing apparatus 100 (not shown) or in a storage region of the integrated circuits.

The display 300 is a 3D display. The display 300 displays a three-dimensional image based on the display image acquired from the image processing apparatus 100. The display 300 is, for example, a 3D display utilizing polarization. In this case, the user can recognize the display image as a three-dimensional image by viewing the image displayed on the display 300 with polarized glasses.

<Operation of Image Processing Apparatus>

Figure 3:
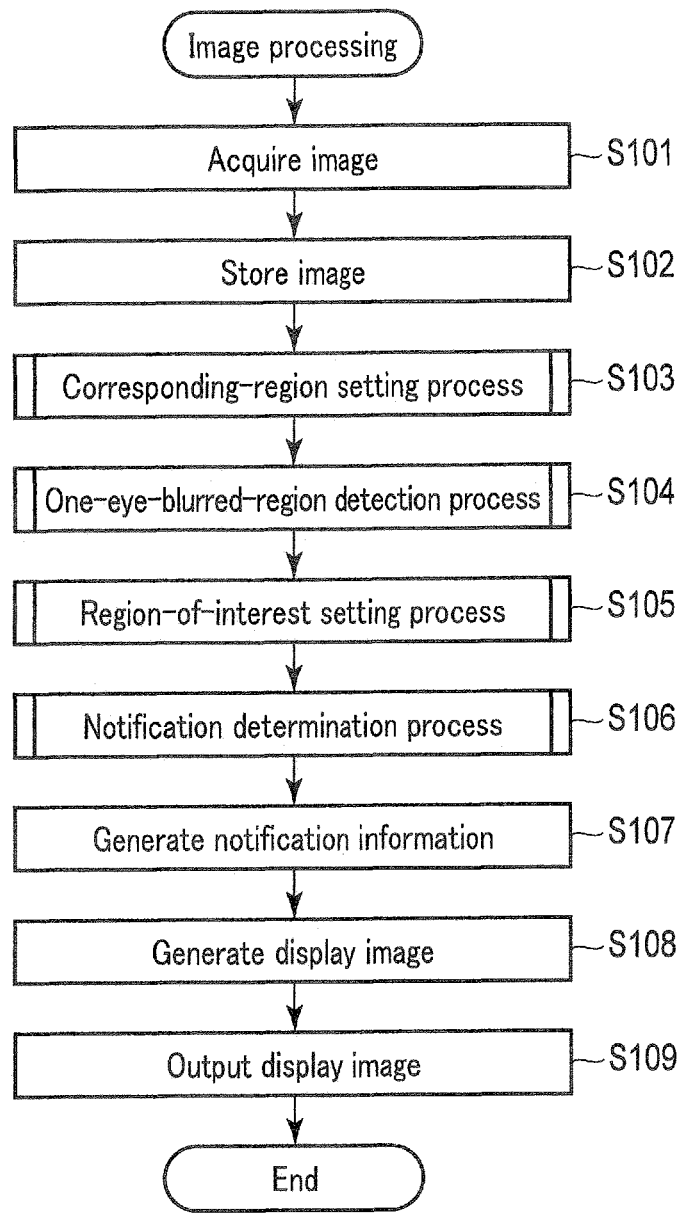
FIG. 3 is a flowchart showing an example of image processing performed by an image processing apparatus according to the first embodiment.

An example of the image processing performed by the image processing apparatus 100 is shown in the form of a flowchart in FIG. 3, and the operation of the image processing apparatus 100 will be described with reference to the flowchart.

In step S101, the image acquisition unit 110 acquires a subject image obtained by imaging from the imaging unit 210 of the endoscope device 200. The subject image acquired in this step includes the left image acquired by the left-image acquisition unit 211 and the right image acquired by the right-image acquisition unit 212. In step S102, the image storage 120 temporarily stores the acquired subject image. At this time, the left image and the right image are stored separately.

Figure 4:
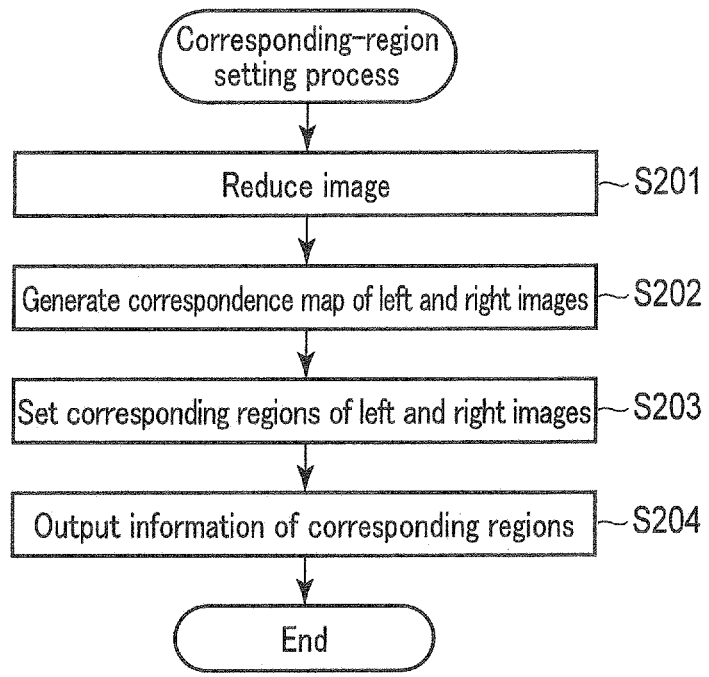
FIG. 4 is a flowchart showing an example of a corresponding-region setting process performed by a corresponding-region generator according to the first embodiment.

In step S103, the corresponding-region generator 131 included in the one-eye-blurred-region setting unit 130 performs a process for setting corresponding regions (corresponding-region setting process). An example of the corresponding-region setting process performed by the corresponding-region generator 131 according to the present embodiment is shown in the form of a flowchart in FIG. 4, to describe the corresponding-region setting process with reference to the flowchart.

In step S201, the corresponding-region generator 131 acquires the left image and the right image from the image storage 120. Also, in order to reduce the computation load in the subsequent image processing, the corresponding-region generator 131 performs image processing for reducing an image on each image to reduce the data amount of each image. The image processing for reducing the image may be omitted. In step S202, the corresponding-region generator 131 generates a correspondence map showing a distribution within the image with respect to the degree of correlation (degree of similarity, degree of difference) between the left image and the right image. Methods such as the SAD (sum of absolute difference) calculation method, POC (phase-only correlation) calculation method, NCC (normalized cross correlation) calculation method may be employed to generate the correspondence map. In step S203, the corresponding-region generator 131 acquires corresponding points of the left image and the right image based on the correspondence map, and sets the corresponding regions of the left image and the right image. Depending on the image state of the left image and the right image, there may be a case where the reliability of the corresponding points obtained based on the correspondence map is low, or a case where the corresponding points cannot be obtained. The image state is based on, for example, the manner and degree of deterioration of the image quality, the subject texture in the image, and the like. The corresponding-region generator 131 according to the present embodiment sets the corresponding regions by interpolating the correspondence map, using the result of the peripheral region when the corresponding points cannot be obtained or when the reliability of the obtained corresponding points is low. In step S204, the corresponding-region generator 131 outputs information related to the set corresponding regions (corresponding-region information) to the one-eye-blurred-region detector 132. Thereafter, the corresponding-region setting process ends, and the process proceeds to step S104 of the image processing shown in FIG. 3.

Figure 5:
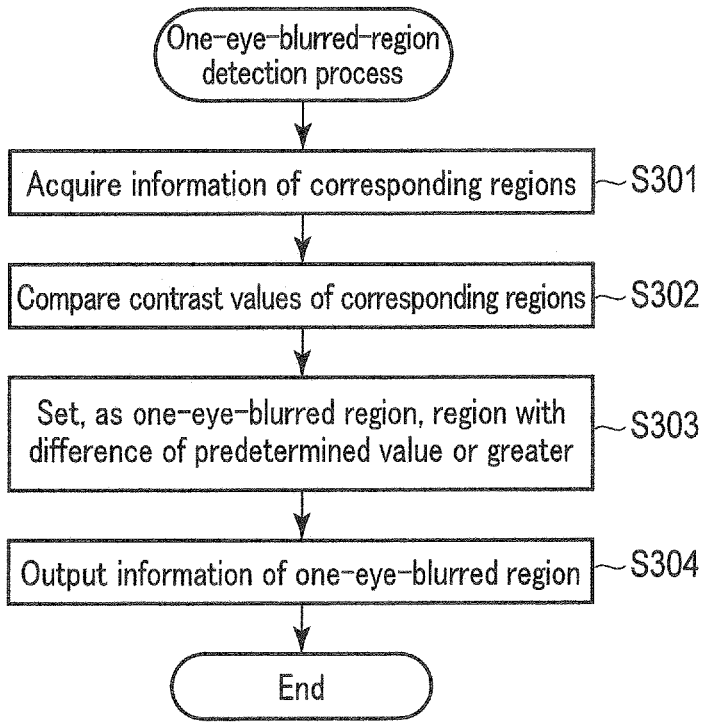
FIG. 5 is a flowchart showing an example of a one-eye-blurred-region detection process performed by a one-eye-blurred-region detector according to the first embodiment.
Figure 6A:
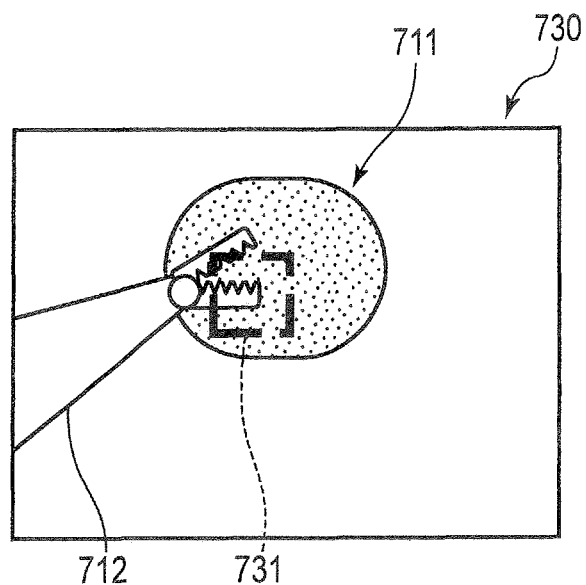
FIG. 6A is a schematic diagram showing an example of the left image to illustrate a comparison of the corresponding regions of the left image and the right image according to the first embodiment.
Figure 6B:
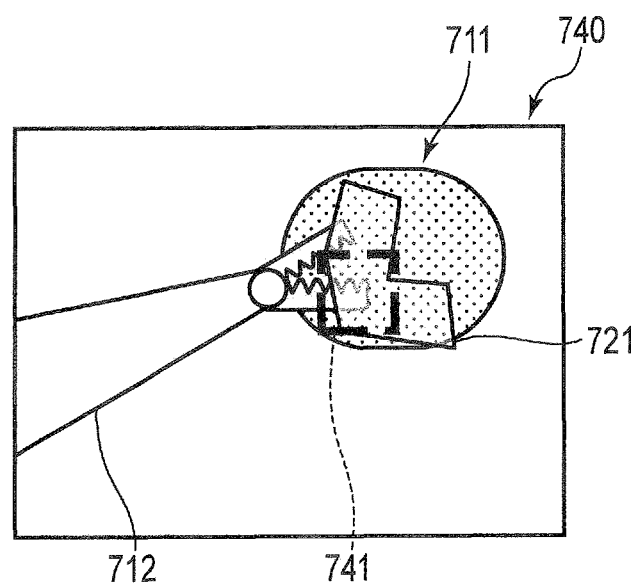
FIG. 6B is a schematic diagram showing an example of the right image to illustrate a comparison of the corresponding regions of the left image and the right image according to the first embodiment.

In step S104, the one-eye-blurred-region detector 132 included in the one-eye-blurred-region setting unit 130 performs a process for detecting the one-eye-blurred region (one-eye-blurred-region detection process) based on, for example, the magnitude of the difference value of the contrast values of the left image and the right image. An example of the one-eye-blurred-region detection process performed by the one-eye-blurred-region detector 132 according to the present embodiment is shown in the form of a flowchart in FIG. 5, and schematic diagrams for illustrating the comparison of the corresponding regions of the left image and the right image according to the present embodiment are shown in FIGS. 6A and 6B, to describe the one-eye-blurred-region detection process with reference to the flowchart and the schematic diagrams.

Figure 7:
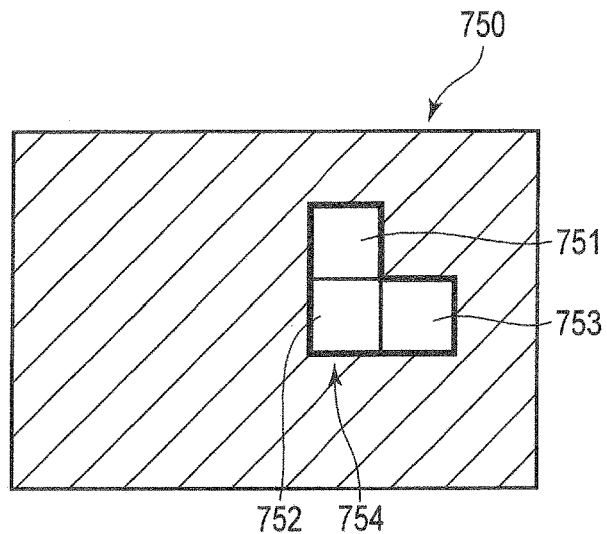
FIG. 7 is a schematic diagram showing an example of one-eye-blurred-region information according to the first embodiment.

In step S301, the one-eye-blurred-region detector 132 acquires corresponding-region information from the corresponding-region generator 131. In step S302, the one-eye-blurred-region detector 132 compares the contrast values of the corresponding regions of the left image 730 and the right image 740 based on the acquired corresponding-region information. For example, the one-eye-blurred-region detector 132 compares the contrast values of the corresponding region 731 of the left image 730 and the corresponding region 741 of the right image 740. The contrast values to be compared in this step are obtained by, for example, applying a band-pass filter to each of pixel values in the corresponding regions and averaging the filtered pixel values in the corresponding regions. It is desirable that the band-pass filter used at this time be designed to pass a band that differentiates the state where there is a blur from the state where there is no blur. Also, not only the average value of the filtered pixel values in the corresponding regions, but also a statistical value, such as a median value of the pixel values in the corresponding regions, may be used. The contrast value may be calculated by a method other than calculation using a band-pass filter, such as through use of an edge amount. In step S303, the one-eye-blurred-region detector 132 sets, as the one-eye-blurred region, a region where the difference value of the contrast values of the corresponding regions is equal to or greater than a predetermined value. For example, the corresponding region 741 of the right image 740 is included in the region 721 where the image is not clear, and the contrast value is lowered. In this manner, the difference between the contrast values of the corresponding regions becomes large in the one-eye-blurred region due to the blurring occurring in only one of the left image 730 and the right image 740. An example of the one-eye-blurred-region information computed from the comparison of the contrast values of the corresponding regions of the left image 730 and the right image 740 is shown in FIG. 7. In FIG. 7, a region where the difference between the contrast values is larger than a predetermined threshold is shown in white, and a region where the difference between the contrast values is smaller than the predetermined threshold is shown in black (hatched). As shown in the image 750 in FIG. 7, the one-eye-blurred-region detector 132 detects a region 751, region 752, and region 753 having a large difference value of the contrast values between the corresponding regions, as a one-eye-blurred region 754. In step S304, the one-eye-blurred-region detector 132 outputs information related to the one-eye-blurred region as one-eye-blurred-region information. Thereafter, the one-eye blurred-region detection process ends, and the process proceeds to step S105 of the image processing shown in FIG. 3.

In step S105, the region-of-interest setting unit 140 performs a region-of-interest setting process of setting a region of interest as a region to be watched by the user. An example of the region-of-interest setting process according to the present embodiment is shown in the form of a flowchart in FIG. 8, to describe the region-of-interest setting process with reference to this flowchart.

Figure 9:
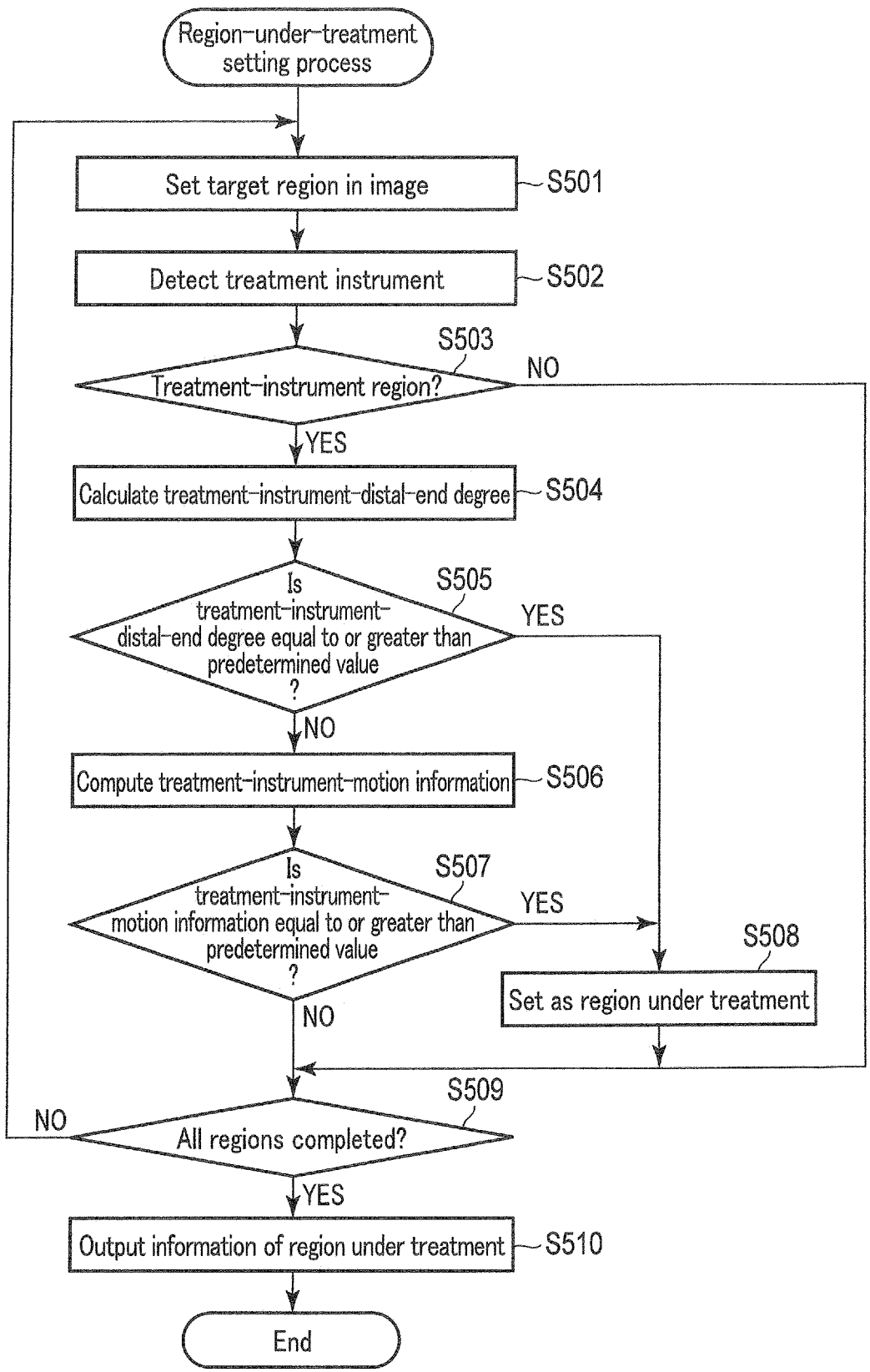
FIG. 9 is a flowchart showing an example of a region-under-treatment setting process according to the first embodiment.

In step S401, the region-of-interest setting unit 140 performs a region-under-treatment setting process of setting a region under treatment. An example of the region-under-treatment setting process according to the present embodiment is shown in the form of a flowchart in FIG. 9, to describe the region-under-treatment setting process with reference to the flowchart.

Figure 10:
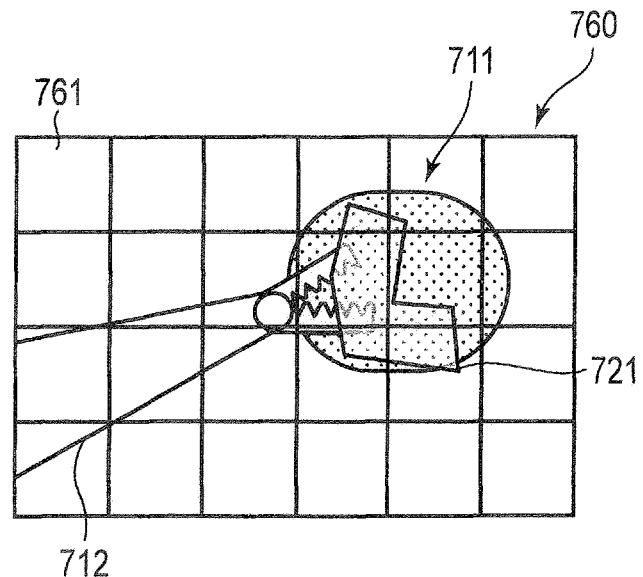
FIG. 10 is a schematic diagram showing an example of a target region according to the first embodiment.

In step S501, the region-under-treatment setting unit 141 included in the region-of-interest setting unit 140 acquires a subject image from the image storage 120. The subject image includes a left image and a right image. The region-under-treatment setting unit 141 divides the left image or right image into regions including at least one pixel, and sets one of the regions of the image divided as a target region. In the present embodiment, a case of dividing the image into rectangular regions is described as an example; however, the present embodiment is not limited thereto. An example of the target region according to the present embodiment is shown in the form of a schematic diagram in FIG. 10. As shown in FIG. 10, the region-under-treatment setting unit 141 divides an image 760 into a plurality of regions such as regions 761.

Figure 11:
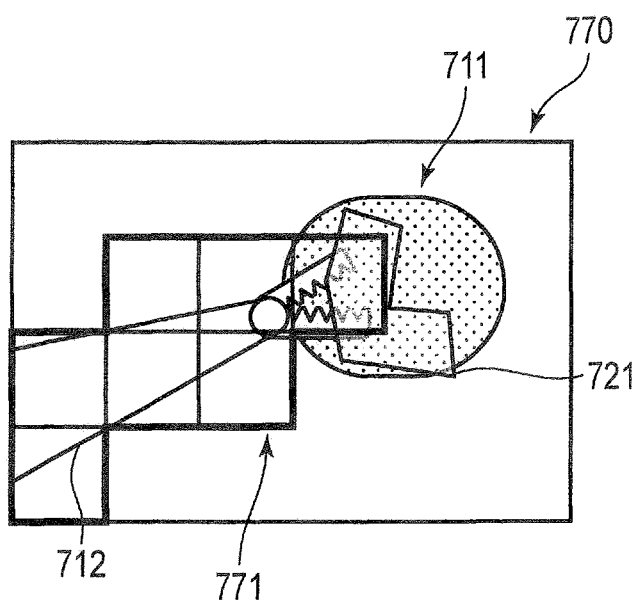
FIG. 11 is a schematic diagram showing an example of a treatment-instrument region according to the first embodiment.

In step S502, the treatment-instrument detector 142 included in the region-under-treatment setting unit 141 detects a treatment instrument such as forceps 712 in the target region. The result of the detection performed on the image 760 shown in FIG. 10 is shown in the form of a schematic diagram in FIG. 11. As shown in FIG. 11, the treatment-instrument detector 142 included in the region-under-treatment setting unit 141 detects a region where there is a treatment instrument such as forceps 712 as a treatment-instrument region 771 in an image 770. Determination of whether or not the target region is the treatment-instrument region 771 is performed using color information. At this time, a value obtained from RGB average values, which include an average value of each of the R value, G value, and B value in the target region, for example, is used to represent the color information. In the determination of whether or not the target region is the treatment-instrument region 771, the target region is determined to be the treatment-instrument region 771, for example, when the ratio of the RGB average values in the target region or the color saturation and hue obtained from the RGB average values in the target region have features different from those of the living body. In the present embodiment, the case where the RGB average values in the target region are used is described as an example; however, the present embodiment is not limited thereto. The color information may be computed, for example, from a median of the R value, G value, and B value in the target region, or from a peak value using a histogram of each of the R value, G value, and B value in the target region.

In step S503, the region-under-treatment setting unit 141 determines whether or not the target region is a region with a treatment instrument. That is, it is determined whether the target region is included in the treatment-instrument region 771. When it is determined that the target region is the treatment-instrument region 771, the region-under-treatment setting process proceeds to step S504, and when it is not determined as such, the process proceeds to step S509.

Figure 12:
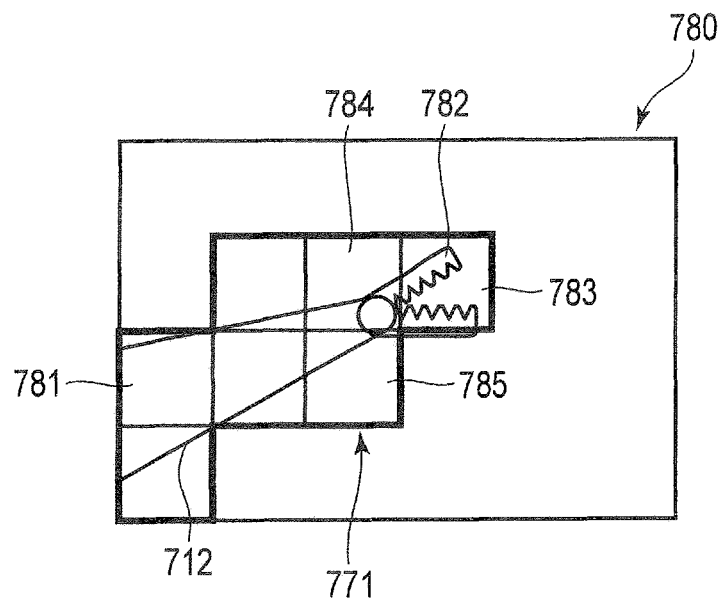
FIG. 12 is a schematic diagram for explaining computation of a degree of being at a distal end of a treatment instrument according to the first embodiment.

In step S504, the region-under-treatment setting unit 141 calculates a degree of being at a distal end of a treatment instrument (referred to as a "treatment-instrument-distal-end degree") for the treatment-instrument region 771. The treatment-instrument-distal-end degree is calculated, for example, based on information related to the shape of a treatment instrument (shape information of a treatment instrument). A schematic diagram for explaining calculation of the treatment-instrument-distal-end degree according to the present embodiment is shown in FIG. 12. In many case of the treatments, a distal end of a treatment instrument is used. Therefore, a region with a high treatment-instrument-distal-end degree can be treated as the region under treatment. In an image 780 shown in FIG. 12, a distal end 782 of forceps 712 is located in a region 783 of the treatment-instrument region 771. The method of calculating the distal-end degree may be performed by counting the number of corners in the treatment-instrument region. Generally, the distal end of the treatment instrument is rounded or has a complicated shape. Therefore, it is possible to determine that the distal-end degree is higher in a region with many corners among the regions included in the treatment-instrument region 771. The corner detection may be performed using a general method such as the Harris corner detection method. The treatment-instrument-distal-end degree may be calculated in accordance with a distance from a start point, the start point being a region at the image end portion among the successive regions included in the treatment-instrument region 771. For example, since the treatment instrument extends from the image end portion toward the organ 711 to be treated in the image 790, the treatment-instrument-distal-end degree can be set according to the distance from the treatment instrument present at the image end portion.

In step S505, the region-under-treatment setting unit 141 determines whether or not there is a region where the treatment-instrument-distal-end degree is equal to or greater than a predetermined value (a distal-end region of the treatment instrument) among the regions included in the treatment-instrument region 771. In regard to the determination, a case will be described as an example below where the treatment-instrument-distal-end degree is determined to be equal to or less than a predetermined value in the region 781, etc., and the treatment-instrument-distal-end degree is determined to be equal to or greater than a predetermined value in the region 783 of the treatment-instrument region 771 shown in FIG. 12, for example. When it is determined that there is a region where the treatment-instrument-distal-end degree is equal to or greater than a predetermined value, the region-under-treatment setting process proceeds to step S508, and when it is not determined as such, the process proceeds to step S506.

Figure 13:
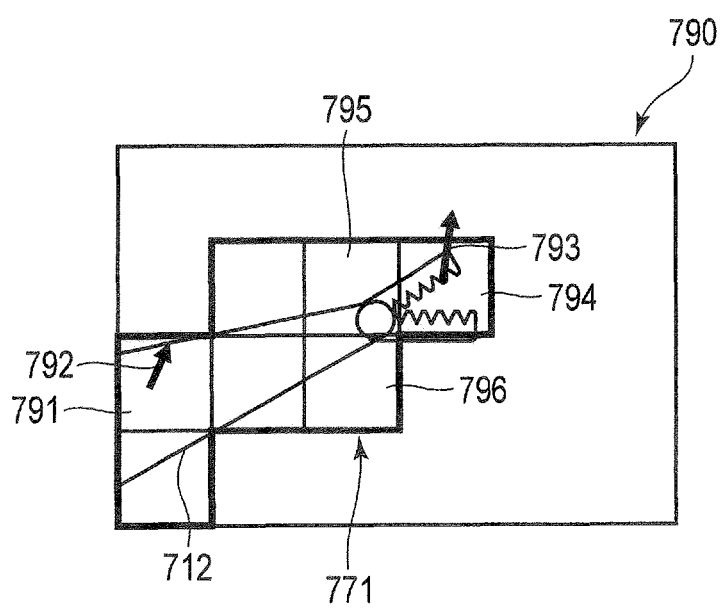
FIG. 13 is a schematic diagram for explaining computation of treatment-instrument-motion information according to the first embodiment.

In step S506, the region-under-treatment setting unit 141 computes treatment-instrument-motion information with respect to the treatment-instrument region 771 in the subject image. The treatment-instrument-motion information is computed from the difference between the current subject image and the past subject image. The past subject image to be used is, for example, an image one frame before the current subject image, and is acquired from the image storage 120. A schematic diagram for explaining computation of the treatment-instrument-motion information according to the present embodiment is shown in FIG. 13. The region-under-treatment setting unit 141 calculates, for example, the amount of movement of the forceps 712 with respect to the treatment-instrument region 771 in the image 790 as the treatment-instrument-motion information. The amount of movement may be calculated using an existing motion vector calculation method. Generally, a treatment instrument such as the forceps 712 is inserted through a channel dedicated for the treatment instrument or an insertion port such as a trocar. Therefore, the movement of a part closer to the insertion port is smaller. For example, in the region 791 in FIG. 13, the amount of movement of the forceps 712 is small, as indicated by the motion vector 792. On the other hand, the movement of a part farther from the insertion port, such as the distal end of the forceps 712, is larger. For example, in the region 794 in FIG. 13, the amount of movement of the forceps 712 is large, as indicated by the motion vector 793.

In step S507, the region-under-treatment setting unit 141 determines whether or not there is a region where the treatment-instrument-motion information is equal to or greater than a predetermined value among the regions included in the treatment-instrument region 771. In regard to the determination, a case will be described as an example below where the treatment-instrument-motion information is determined to be equal to or less than a predetermined value in the region 791, etc., and the treatment-instrument-motion information is determined to be equal to or greater than a predetermined value in the regions 794, 795, and 796 of the treatment-instrument region 771 shown in FIG. 13, for example. However, since the region 794 corresponds to, for example, the region 783 where the treatment-instrument-distal-end degree is determined to be equal to or greater than a predetermined value in step S505, the processing of this step is not performed on the region 794. When it is determined that there is a region where the treatment-instrument-motion information is equal to or greater than a predetermined value, the region-under-treatment setting process proceeds to step S508, and when it is not determined as such, the process proceeds to step S509.

In the present embodiment, the case where the region-under-treatment setting unit 141 uses the amount of movement as the motion information is described as an example; however, the present embodiment is not limited thereto. For example, the region-under-treatment setting unit 141 may obtain variation of the movement of the treatment instrument in the region. Since the treatment instrument performs an operation such as grasping and cutting the living body at the distal end, there will be multiple movement directions. If the variation of the movement between the target region and a region around the target region is equal to or greater than a predetermined value, the target region may be set as the region of interest. Alternatively, small regions may be created in the target region to observe the variation of the movement. The treatment-instrument-motion information may not be determined based on a single criterion, and may be computed based on multiple pieces of information such as a combination of the amount of movement and the variation of the movement described above.

Figure 14:
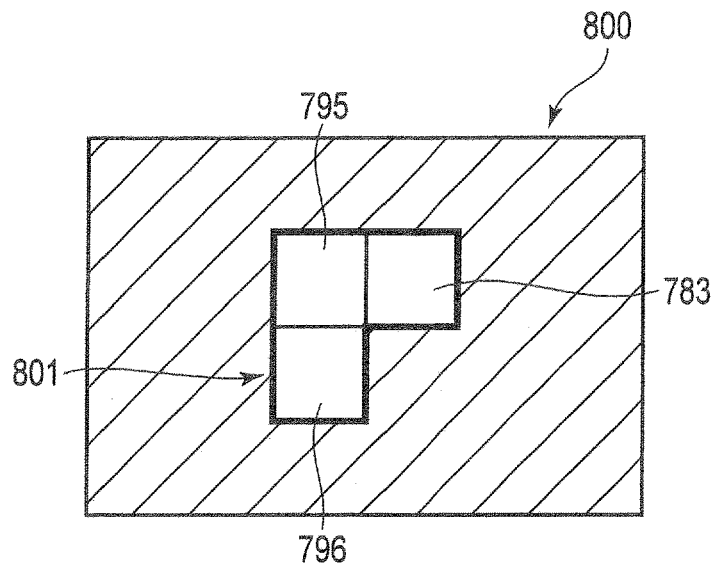
FIG. 14 is a schematic diagram showing an example of region-under-treatment information according to the first embodiment.

In step S508, the region-under-treatment setting unit 141 sets, as a region under treatment, the region where the treatment-instrument-distal-end degree is determined to be equal to or greater than a predetermined value in step S505, or the region where the treatment-instrument-motion information is determined to be equal to or greater than a predetermined value in step S507. An example of the information related to the region under treatment (region-under-treatment information) according to the present embodiment is shown in the form of a schematic diagram in FIG. 14. In FIG. 14, the region set as a region-under-treatment 801 is shown in white, and the region not set as the region-under-treatment 801 is shown in black (hatched). As shown in the image 800 in FIG. 14, the region-under-treatment setting unit 141 according to the present embodiment sets, as the region-under-treatment 801, the region 783 selected based on the treatment-instrument-distal-end degree and the regions 795 and 796 selected based on the treatment-instrument-motion information. Thereafter, the region-under-treatment setting process proceeds to step S509.

In step S509, the region-under-treatment setting unit 141 determines whether or not the determination based on the treatment-instrument-distal-end degree and the treatment-instrument-movement amount has been performed for all the regions included in the treatment-instrument region 771 (whether or not the determination has been completed for all the regions). If it is not determined that the determination has been completed for all the regions, the region-under-treatment setting process returns to step S501, and the operations in steps S501 to S509 are repeated until it is determined that the determination has been completed for all the regions. If it is determined that the determination has been completed for all the regions, the region-under-treatment setting process proceeds to step S510.

In step S510, the region-under-treatment setting unit 141 outputs information related to the region-under-treatment 801 as the region-under-treatment information. Thereafter, the region-under-treatment setting process ends, and the process proceeds to step S402 of the region-of-interest setting process shown in FIG. 8.

In the present embodiment, the region-under-treatment setting process, in which the determination based on the treatment-instrument-motion information is performed when the treatment-instrument-distal-end degree is not determined to be equal to or greater than a predetermined value in the determination based on the treatment-instrument-distal-end degree, is described as an example; however, the present embodiment is not limited thereto. In the region-under-treatment setting process, for example, the determination based on the treatment-instrument-distal-end degree may be performed after the determination based on the treatment-instrument-motion information is performed, or only one of the determination based on the treatment-instrument-distal-end degree or the determination based on the treatment-instrument-motion information may be performed.

In step S402, the region-of-interest setting unit 140 performs an operation of selecting a determination-target region, in which a region to be determined for its setting or otherwise as a region of interest is selected. In the operation of selecting a determination-target region, the region-of-interest setting unit 140 sequentially selects each target region set in the image 760 in the region-under-treatment setting process illustrated in FIG. 10, for example.

In step S403, the region-of-interest setting unit 140 determines whether or not the determination-target region selected in step S402 is a region set as the region-under-treatment in the region-under-treatment setting process. That is, the determination can also be expressed as determination of whether or not the determination-target region is included in the region-under-treatment 801. When it is determined that the region is set as the region-under-treatment, the region-of-interest setting process proceeds to step S404, and when it is not determined as such, the process proceeds to step S405.

In step S404, the region-of-interest setting unit 140 sets, as the region of interest, the determination-target region set as the region under treatment in the region-under-treatment setting process.

In step S405, the region-of-interest setting unit 140 determines whether or not the operations in steps S402 to S404 have been completed for all the regions in the target region set in the image 760. When it is determined that the operations have been completed for all the regions, the region-of-interest setting process proceeds to step S406, and when it is not determined as such, the process returns to step S402.

In step S406, the region-of-interest setting unit 140 outputs the information related to the region of interest to the notification determination unit 150 as region-of-interest information. In the present embodiment, since the region under treatment is set as the region of interest, the region-under-treatment information shown in the image 800 in FIG. 14, for example, is output as the region-of-interest information of the present embodiment. Thereafter, the region-of-interest setting process ends, and the process proceeds to step S106 of the image processing illustrated in FIG. 3.

In the present embodiment, the case where the region-under-treatment 801 is set as the region of interest is described as an example; however, the present embodiment is not limited thereto. For example, when there is no region under treatment, as in the case of observation without treatment, central-position information may be acquired for each of the left image and the right image, so that a certain proportion of a region including the center of each image (a region that accounts for a certain proportion around the center of the image) may be set as the region of interest.

Figure 15:
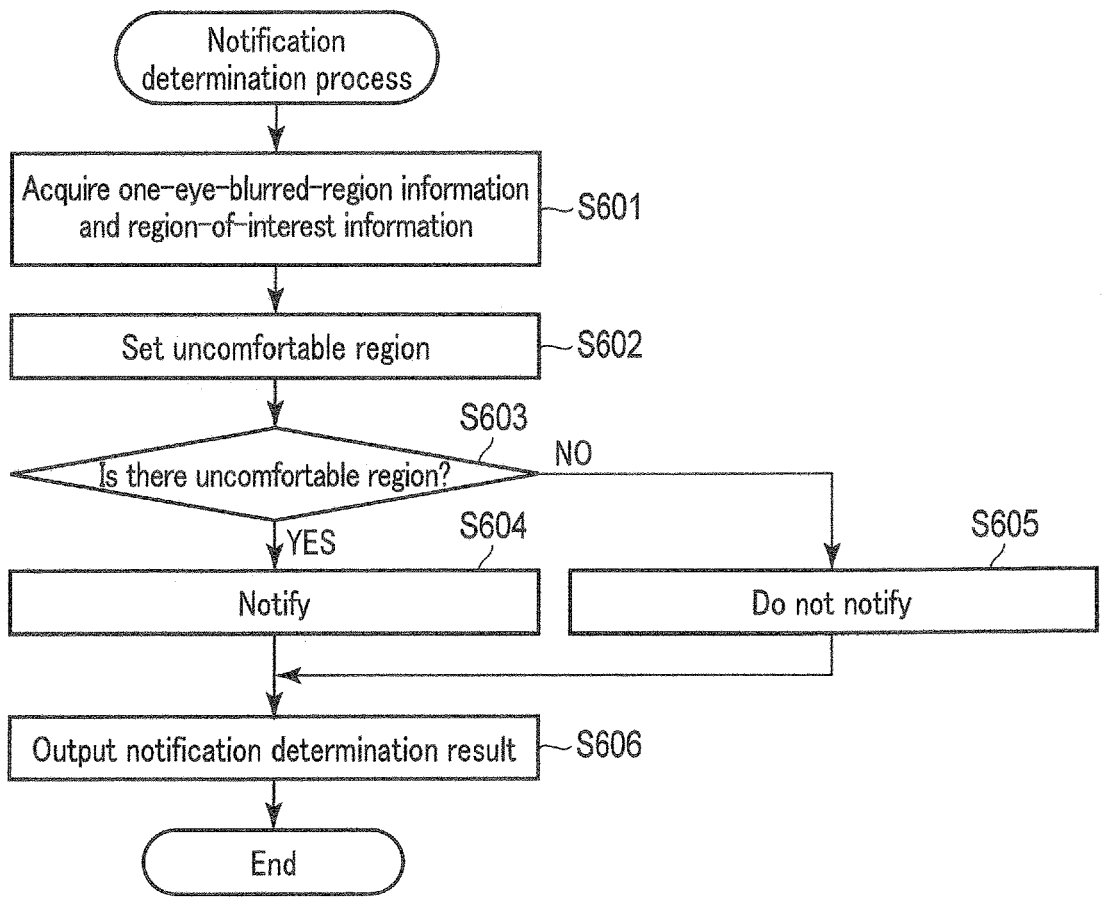
FIG. 15 is a flowchart showing an example of a notification determination process according to the first embodiment.

In step S106, the notification determination unit 150 performs a notification determination process. An example of the notification determination process according to the present embodiment is shown in the form of a flowchart in FIG. 15, to describe the notification determination process with reference to the flowchart.

In step S601, the notification determination unit 150 acquires one-eye-blurred-region information shown in FIG. 7 from the one-eye-blurred-region setting unit 130, and acquires region-of-interest information shown in FIG. 14 from the region-of-interest setting unit 140.

In step S602, the notification determination unit 150 sets an uncomfortable region based on the one-eye-blurred-region information and the region-of-interest information. The notification determination unit 150 sets, as the uncomfortable region, a region where a part or whole of the one-eye-blurred region overlap with a part or whole of the region of interest. The setting of the uncomfortable region according to the present embodiment will be described with reference to the schematic diagrams shown in FIGS. 16 and 17. In FIG. 16, the region set as the one-eye-blurred region or the region of interest is shown in white, and the region not set as such is shown in black (hatched). As shown in the image 810 in FIG. 16, the notification determination unit 150 according to the present embodiment detects, as the uncomfortable region 811, a region where the one-eye-blurred region 754 and the region of interest overlap each other (the region surrounded by a broken line). Also, in FIG. 17, the region set as the uncomfortable region 811 is shown in white, and the region not set as the uncomfortable region 811 is shown in black (hatched). The notification determination unit 150 outputs the information related to the detected uncomfortable region 811 as uncomfortable-region information, as shown in the image 820 (uncomfortable-region image) in FIG. 17.

In step S603, the notification determination unit 150 determines whether or not the uncomfortable region 811 is detected in step S602. When it is determined that the uncomfortable region 811 is detected, the notification determination process proceeds to step S604, and when it is not determined as such, the process proceeds to step S605.

In step S604, the notification determination unit 150 determines that the user is to be notified that the uncomfortable region 811 exists and the three-dimensional image based on the current left image and right image may give the user a sense of discomfort.

In step S605, the notification determination unit 150 determines that the notification is not given to the user because the uncomfortable region 811 does not exist.

In step S606, the notification determination unit 150 outputs the result of the determination performed in step S604 or step S605 to the notification-information generator 160 as a notification determination result. Thereafter, the notification determination process ends, and the process proceeds to step S107 of the image processing illustrated in FIG. 3.

In step S107, the notification-information generator 160 generates information to be reported to the user. The notification-information generator 160 according to the present embodiment generates a notification image to notify the user of positional information of the uncomfortable region as well. An example of the notification image according to the present embodiment is shown in the form of a schematic diagram in FIG. 18. The notification-information generator 160 generates, as the notification image, a correlation image 830 in which a frame representing the uncomfortable region 811 is superimposed on the image in which the uncomfortable region is detected, as shown in FIG. 18, for example. The notification image generated by the notification-information generator 160 is not limited to the correlation image 830, and may be, for example, a message image indicating that one of the lenses is dirty. Also, the notification information generated by the notification-information generator 160 is not limited to an image, and may be a sound or both of the image and the sound. Furthermore, the notification information may be a control signal for changing the color of the frame of the image when each of the left image and the right image is displayed on the display 300. When the notification image is generated by the notification-information generator 160, it is preferable that the size of the generated notification image be smaller than the size of the left image and the right image. It is even more preferably one-ninth the size of the left image or the right image.

Figure 19A:
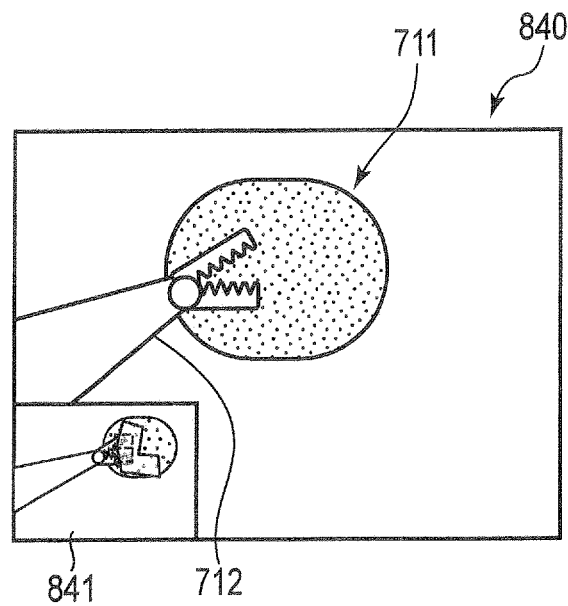
FIG. 19A is a schematic diagram showing an example of a display image of the left image according to the first embodiment.
Figure 19B:
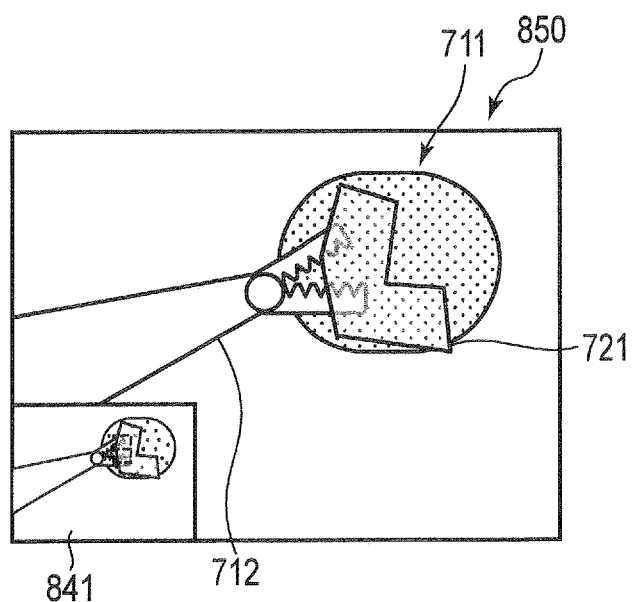
FIG. 19B is a schematic diagram showing an example of a display image of the right image according to the first embodiment.

In step S108, the display-image generator 170 generates display information including the display image to be output to the display 300. An example of the display image of the left image 840 is shown in the form of a schematic diagram in FIG. 19A, and an example of the display image of the right image 850 is shown in the form of a schematic diagram in FIG. 19B. As shown in FIGS. 19A and 19B, the display-image generator 170 according to the present embodiment superimposes the notification image 841 generated by the notification-information generator 160 on each of the left image 840 and the right image 850 obtained from the image storage 120. The display position of the notification image 841 in the display images (the left image 840 and the right image 850) is, for example, a position that does not overlap with the region of interest. Displaying the notification image 841 at a position not overlapping with the region of interest in this manner prevents the user from being obstructed.

The display position and the display size of the notification image 841 in the display images (the left image 840 and the right image 850) are not limited to the above-described position and size. The display position and the display size of the notification image 841 in the display images are those that do not obstruct the user's view, and may be a position and a size that can be recognized by the user. The notification image 841 included in the display images is, for example, the correlation image 830, as shown in FIGS. 19A and 19B, but is not limited thereto. The notification image 841 may be an image (notification information) that can report that one-eye blurring has occurred, as described above.

In step S109, the display-image generator 170 outputs the generated display images (the left image 840 and the right image 850) to the display 300. Thereafter, the image processing ends.

<Advantages of Endoscope System>

As described above, the image processing apparatus 100 according to the present embodiment detects the one-eye-blurred region in which one-eye blurring is occurring and the region of interest to which the user is paying attention. When there is an overlapping region (uncomfortable region) between the one-eye-blurred region and the region of interest, the image processing apparatus 100 according to the present embodiment determines that the user is to be notified of such.

On the other hand, the image processing apparatus 100 according to the present embodiment determines that the user is not notified of such because the user does not easily feel a sense of discomfort when one-eye blurring occurs in a region in a subject image, such as an image peripheral portion not under treatment, that is either unimportant or not the focus of the user's attention.

As described above, since the image processing apparatus 100 considers the region of interest of the user in the treatment using a three-dimensional endoscope, the endoscope system 1 according to the present embodiment can notify the user only when one-eye blurring causes a sense of discomfort.

In particular, when a treatment is performed using a three-dimensional endoscope, one-eye blurring is likely to occur due to contact with the living body, water or oil remaining in the space, or the like. Therefore, with the technology disclosed above, the notification is not performed when it is unnecessary to do so, and therefore the user is not prevented from performing treatment by frequent notification and can avoid fatigue caused by one-eye blurring by virtue of proper notification.

Second Embodiment

A second embodiment will be described. Hereinafter, the differences from the first embodiment will be described. The same parts as those described in the first embodiment will be denoted by the same reference signs, and a description of those parts will be omitted.

In the first embodiment, the endoscope system 1, including the image processing apparatus 100 in which the region under treatment detected by the region-under-treatment setting unit 141 is set as the region of interest, is described. On the other hand, when a treatment is being performed under an endoscope, not only the treatment instrument but also the living body to be treated may be focused on. Therefore, in the present embodiment, the endoscope system 1 including the image processing apparatus 100, that is capable of setting a region targeted for treatment as a region of interest, will be described.

<Configuration of Endoscope System>

Figure 20:
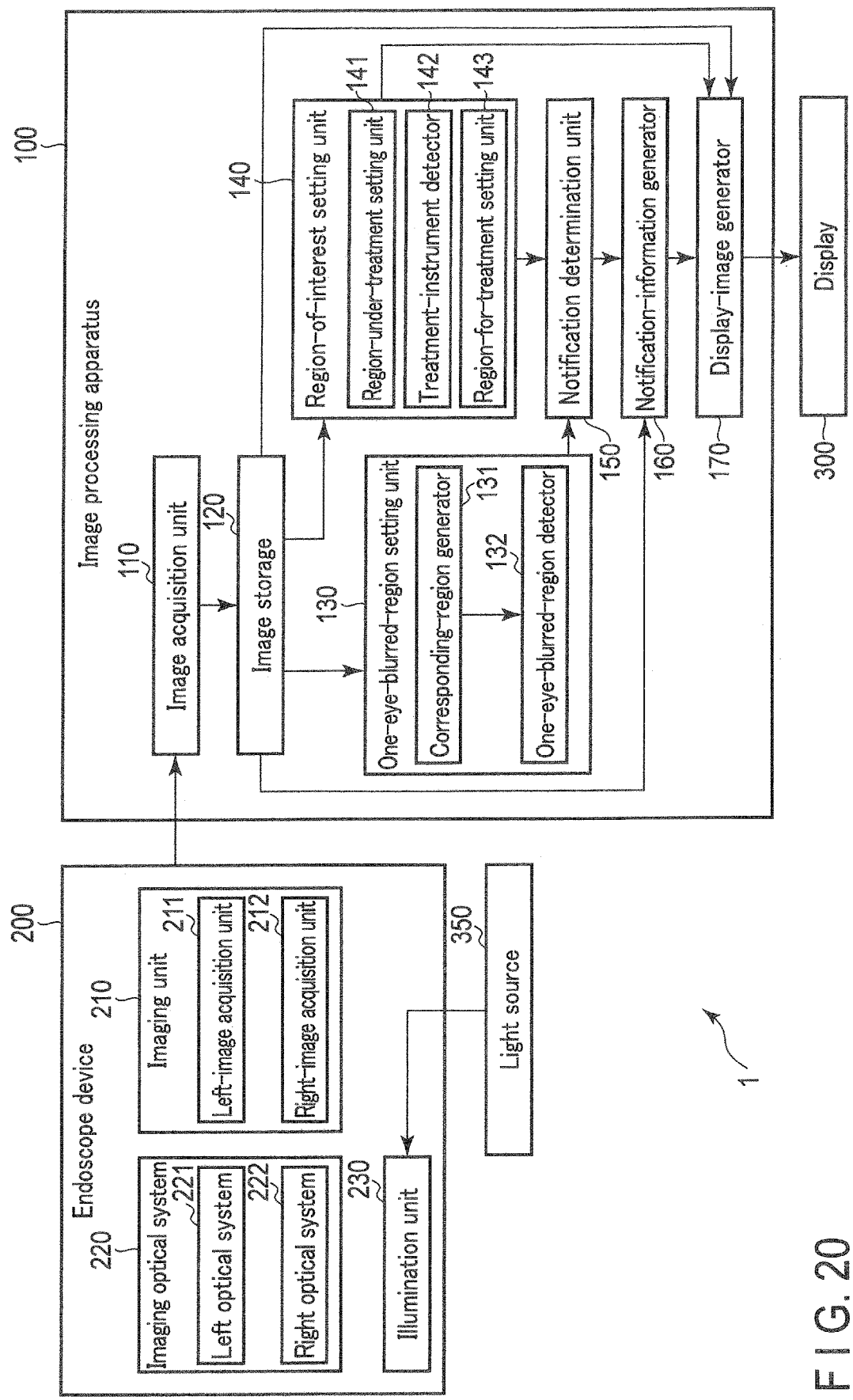
FIG. 20 is a block diagram showing an outline of a configuration example of an endoscope system according to a second embodiment.

An outline of a configuration example of the region-of-interest setting unit 140 included in the image processing apparatus 100 according to the present embodiment is shown in the form of a block diagram in FIG. 20. As shown in FIG. 20, the region-of-interest setting unit 140 according to the present embodiment further includes a region-for-treatment setting unit 143 that sets a region targeted for treatment as a region for treatment (or a fifth region). Since the living body to be treated often exists near the distal end of the treatment instrument, the region-for-treatment setting unit 143 sets, as the region for treatment, a region having features of the living body (living body region) in the vicinity of the region under treatment.

<Operation of Endoscope System>

Figure 21:
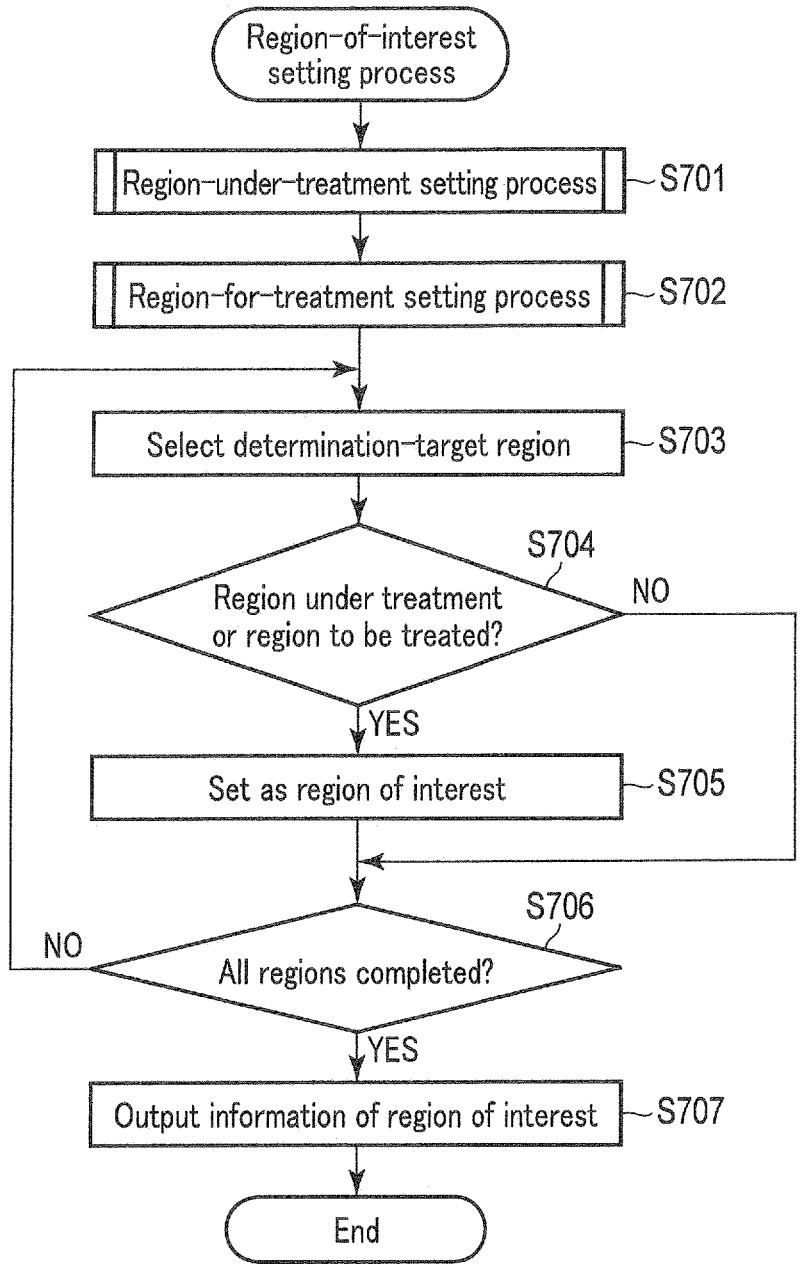
FIG. 21 is a flowchart showing an example of a region-of-interest setting process according to the second embodiment.

An example of the region-of-interest setting process performed by the region-of-interest setting unit 140 according to the present embodiment is shown in the form of a flowchart in FIG. 21, and an operation of the image processing apparatus 100 will be described with reference to the flowchart. The region-of-interest setting process according to the present embodiment is performed, for example, in step S105 of the image processing shown in FIG. 3.

In step S701, the region-of-interest setting unit 140 causes the region-under-treatment setting unit 141 to perform a region-under-treatment setting process. The region-under-treatment setting process is similar to, for example, the region-under-treatment setting process of the first embodiment described with reference to FIG. 9.

Figure 22:
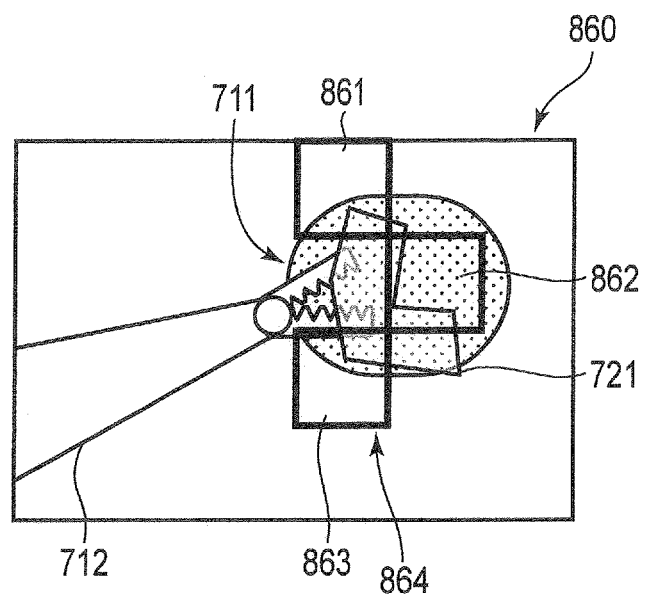
FIG. 22 is a schematic diagram showing an example of a region for treatment according to the second embodiment.

In step S702, the region-of-interest setting unit 140 causes the region-for-treatment setting unit 143 to perform a region-for-treatment setting process. In the region-for-treatment setting process, the setting of the region for treatment is preferably performed at least in the vicinity of a region with the highest treatment-instrument-distal-end degree. In the region-for-treatment setting process, the region-for-treatment setting unit 143 computes the features of the living body from the color information. At this time, the region-for-treatment setting unit 143 computes a region having a feature of a color close to that of the living body using the color saturation or the hue, or both the color saturation and the hue. Also, the region-for-treatment setting unit 143 may compute a color feature for a region near the region with the highest treatment-instrument-distal-end degree, and set a region having a color feature similar to the computed color feature as the region for treatment. An example of the region for treatment according to the present embodiment set in this manner is shown in the form of a schematic diagram in FIG. 22. The region-for-treatment setting unit 143 according to the present embodiment sets the following regions among the plurality of divided regions included in the image 860 as a region-for-treatment 864: the region 861, region 862, and region 863 near the distal end of the forceps 712 (i.e., adjacent to the treatment-instrument region) where the organ 711 (living body) is imaged, as shown in FIG. 22, for example.

Figure 8:
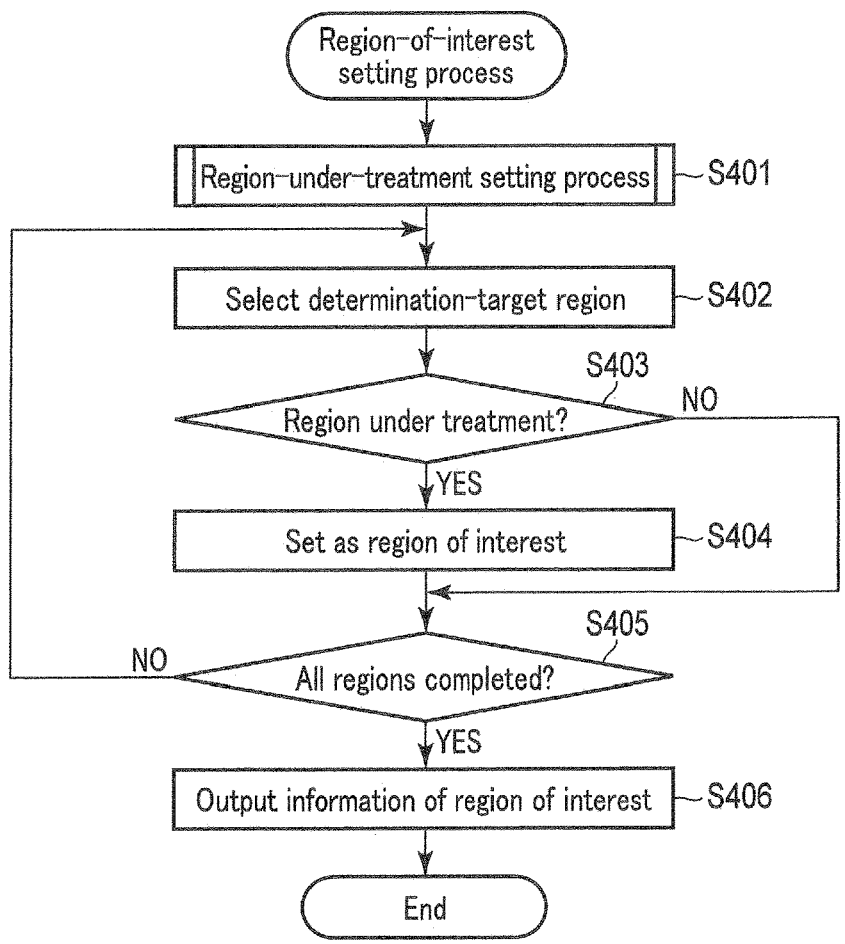
FIG. 8 is a flowchart showing an example of a region-of-interest setting process according to the first embodiment.

In step S703, the region-of-interest setting unit 140 performs an operation of selecting a determination-target region in which a region to be determined as for setting or otherwise as a region of interest is selected, in a manner similar to step S402 of the region-of-interest setting process of the first embodiment shown in FIG. 8, for example.

In step S704, the region-of-interest setting unit 140 determines whether or not the determination-target region selected in step S703 is a region set as at least one of the region-under-treatment 801 or the region-for-treatment 864. That is, the determination can also be expressed as determination of whether or not the determination-target region is included in at least one of the region-under-treatment 801 or the region-for-treatment 864. When it is determined that the region is a region set as at least one of the region-under-treatment 801 or the region-for-treatment 864, the region-of-interest setting process proceeds to step S705, and when it is not determined as such, the process proceeds to step S706.

In step S705, the region-of-interest setting unit 140 sets, as the region of interest, the determination-target region determined as a region set as at least one of the region-under-treatment 801 or the region-for-treatment 864.

In step S706, the region-of-interest setting unit 140 determines whether or not the operations in steps S703 to S705 have been completed for all the regions in the target region. When it is determined that the operations have been completed for all the regions, the region-of-interest setting process proceeds to step S707, and when it is not determined as such, the process returns to step S703.

Figure 23:
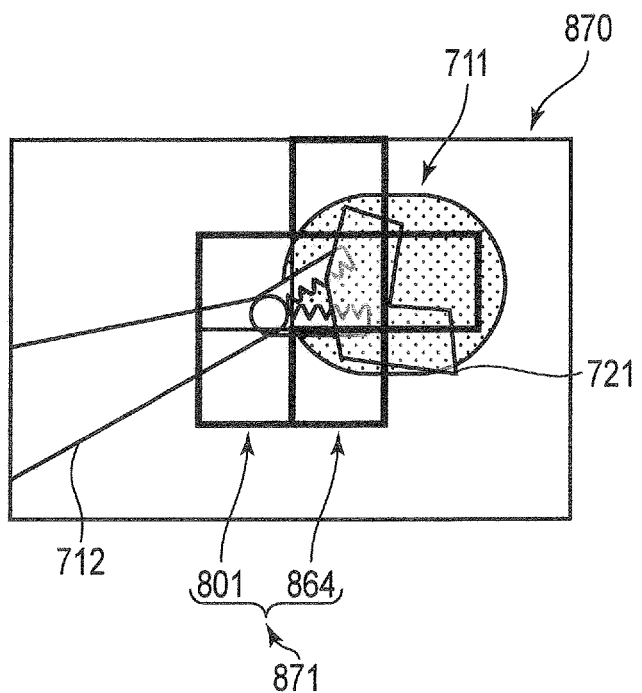
FIG. 23 is a schematic diagram showing an example of a region of interest according to the second embodiment.

In step S707, the region-of-interest setting unit 140 outputs the information related to the set region of interest as region-of-interest information. An example of the region of interest according to the present embodiment is shown in the form of a schematic diagram in FIG. 23. The region-of-interest setting unit 140 according to the present embodiment sets, as a region-of-interest 871, a combination of the region-under-treatment 801 shown in FIG. 14 and the region-for-treatment 864 shown in FIG. 22 among the plurality of divided regions included in the image 870, as shown in FIG. 23, for example.

If only one of the region-under-treatment 801 or the region-for-treatment 864 is detected, only the detected region may be set as the region of interest; and if neither of them is detected, a central portion of the image may be set as the region of interest.

<Advantages of Endoscope System>

The image processing apparatus 100 according to the present embodiment has the following advantages in addition to those achieved in the first embodiment.

The region-of-interest setting unit 140 included in the image processing apparatus 100 according to the present embodiment sets the region-for-treatment 864 in addition to the region-under-treatment 801, and sets a combination of the region-under-treatment 801 and the region-for-treatment 864 as the region of interest. As described above, in the endoscope system 1 according to the present embodiment, the notification is not performed when it is unnecessary to do so, even when the treatment instrument is not within the field of view of the user, that is, even when the user is paying attention to and observing the living body to be treated; therefore, the user is not prevented from performing treatment by frequent notification and can avoid fatigue caused by one-eye blurring by virtue of proper notification.

Third Embodiment

A third embodiment will be described. Hereinafter, the differences from the first embodiment will be described. The same parts as those described in the first embodiment will be denoted by the same reference signs, and a description of those parts will be omitted.

The region-of-interest setting unit 140 according to the first embodiment sets, as a region of interest, all the regions under the condition exceeding a predetermined value. On the other hand, the region-of-interest setting unit 140 according to the present embodiment calculates a degree of interest for each region in order to further narrow the region of interest.

The region-of-interest setting unit 140 according to the present embodiment sets the region of interest in the same manner as in the first embodiment.

Thereafter, the region-of-interest setting unit 140 according to the present embodiment calculates the degree of interest for each of the divided regions included in the region of interest by using at least one or more of the following pieces of information: the distance from the image center; the treatment-instrument-motion information; and the treatment-instrument-distal-end degree (the degree of being a distal end with respect to the shape of the treatment instrument). When calculating the degree of interest using the distance from the image center, the region-of-interest setting unit 140 sets the degree of interest to be higher, for example, as the distance from the central coordinate to the divided region becomes shorter. When calculating the degree of interest using the treatment-instrument-motion information, the region-of-interest setting unit 140 sets the degree of interest to be higher, for example, as the movement amount of the treatment instrument becomes higher. When calculating the degree of interest using the treatment-instrument-distal-end degree, the region-of-interest setting unit 140 sets the degree of interest to be higher, for example, as the treatment-instrument-distal-end degree becomes higher.

The notification determination unit 150 according to the present embodiment determines whether or not there is a region (uncomfortable region) where a region having a high degree of interest in the region of interest and the one-eye-blurred region overlap each other, and determines whether or not to notify the user.

As described above, the image processing apparatus 100 according to the present embodiment determines whether or not to notify the user based on the region having a high degree of interest in the region of interest. Therefore, the endoscope system 1 according to the present embodiment can improve the accuracy of the notification determination process, thus allowing the notification to the user to be performed at a more appropriate timing and frequency.

The image processing apparatus 100 according to the present embodiment may calculate the degree of interest for each of the divided regions included in the uncomfortable region (overlapping region), and determine whether or not to notify the user based on the degree of interest of the overlapping region.

The image processing apparatus 100 according to the present embodiment and the image processing apparatus 100 according to the second embodiment may be combined. That is, in the third embodiment as well, the region of interest may include both the region under treatment and the region for treatment.

Fourth Embodiment

A fourth embodiment will be described. Hereinafter, the differences from the first embodiment will be described. The same parts as those described in the first embodiment will be denoted by the same reference signs, and a description of those parts will be omitted.

In the first embodiment, the image processing apparatus 100, in which the notification determination unit 150 determines to notify the user unconditionally when there is an uncomfortable region, is described. On the other hand, even if there is an uncomfortable region, the user may not be concerned about this. In such a case, it is better not to notify the user so that the user is not interrupted.

The notification determination unit 150 included in the image processing apparatus 100 according to the present embodiment includes a degree-of-discomfort calculation unit. The degree-of-discomfort calculation unit calculates the degree of discomfort using at least one or more of the following pieces of information: the size of the uncomfortable region; the contrast difference between the uncomfortable region and a region in another image corresponding to the uncomfortable region (hereinafter referred to as a "contrast difference between the uncomfortable regions"); and the degree of interest of the uncomfortable region. The notification determination unit 150 according to the present embodiment performs notification determination based on the information of the degree of discomfort calculated by the degree-of-discomfort calculation unit.

In the case of using the size of the uncomfortable region to calculate the degree of discomfort, the notification determination unit 150 determines to make a notification when the size of the uncomfortable region is equal to or greater than a predetermined value. Since humans do not notice blurring in a region that is too small, it is desirable to set, for the predetermined value, a size of region at which blurring can be recognized by humans.

In the case of using the contrast difference between the uncomfortable regions to calculate the degree of discomfort, the notification determination unit 150 determines to make a notification when the contrast difference is equal to or greater than a predetermined value. Since it is difficult for humans to feel a sense of discomfort when the decrease in contrast due to blurring is small, it is desirable to set, for the predetermined value, a numerical value of the contrast difference at which humans feel a sense of discomfort.

In the case of using the degree of interest of the uncomfortable region to calculate the degree of discomfort, the notification determination unit 150 determines to make a notification when the degree of interest is equal to or greater than a predetermined value. For example, the degree of interest of the region of interest described above in the third embodiment, which is used to set the uncomfortable region, may be used for the degree of interest of the uncomfortable region.

As described above, the image processing apparatus 100 according to the present embodiment calculates the degree of discomfort in consideration of the degree of discomfort felt by the user, and determines whether or not to notify the user based on the degree of discomfort. Accordingly, in the endoscope system 1 of the present embodiment, the performance of the determination of notification is improved by, for example, the withholding of a notification when the one-eye blur that occurs is not to the degree at which a user becomes concerned, that is, when the one-eye blur that is detected has a low degree of discomfort; and therefore, the user is not prevented from performing treatment by frequent notification and can avoid fatigue caused by one-eye blurring by virtue of proper notification.

The image processing apparatus 100 of the present embodiment may be combined with at least one of the image processing apparatus 100 of the second embodiment or the image processing apparatus 100 of the third embodiment.

[Modifications]

In the above-described embodiments, the case where the endoscope device 200 is a rigid scope for medical use is described as an example; however, the endoscope device 200 may also be applied to flexible endoscopes for medical use. In addition, the endoscope device 200 may be applied not only to medical endoscopes but also to industrial endoscopes. In this case, a working region may be set instead of the region under treatment based on, for example, an instrument used together with an industrial endoscope, and the uncomfortable region may be set as in the above-described embodiments. Also, the endoscope device 200 may be used in a way that an observation target and the instrument used together with the industrial endoscope are distinguished from each other on an image, based on features such as color.

The setting of the region of interest, the setting, etc., of the uncomfortable region, the setting of the degree of discomfort, the determination of notification, etc., in the image processing described in the above embodiments are mere examples of the determination method, and various other determination methods may be adopted. In various determination methods, not only a simple determination based on a threshold value or the like as in the above-described embodiments, but also a determination based on artificial intelligence (AI) constructed by machine learning such as deep learning, for example, may be employed. The function of the AI is built on a DSP, for example, which is provided inside the image processing apparatus 100. When the image processing apparatus 100 has a communication function, the function of the AI may be provided on, for example, a data server outside the endoscope system 1. For example, the AI learns a region under treatment in a treatment images (subject images) acquired by the endoscope device 200. With such a configuration, the AI can properly detect the region under treatment that the AI learned, therefore allowing the endoscope system 1 to properly notify the user.

Among the techniques described in the above embodiments, the controls described with reference to the flowcharts may be implemented using a program. This program may be implemented in a circuit such as an FPGA. Also, when the program is operated in a CPU or the like, the program may be stored in, for example, a recording medium or a recording unit. There are various methods of recording on the recording medium or the recording unit, such as recording at the time of product shipment, recording using a distributed recording medium, and downloading via the Internet.

In addition, the image processing apparatus 100 according to each embodiment may be applied not only to the endoscope device 200 but also to microscopes, industrial devices for inspection or for other purposes, various medical observation apparatuses, and the like.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An image processing apparatus for an endoscope, the apparatus comprising processing circuitry configured to:
    acquire a pair of a left image and right image;
    generate a three-dimensional display image for three-dimensional observation by a user based on the pair of the left image and right image;
    set a first region in a part of one of the left image and the right image, the first region being a region having a blur;
    set a second region in a part of each of the left image and the right image, the second region being a region where the user is performing treatment, wherein the processing circuitry is configured to set the second region based on a third region set by using at least one of motion information of a treatment instrument used by the user, position information of the treatment instrument on each of the left image and the right image, and shape information of the treatment instrument;
    determine whether or not the first region at least partially overlaps with the second region;

in response to determining that the first region at least partially overlaps with the second region, outputting a notification to the user; and in response to determining that the first region does not at least partially overlap with the second region, not outputting the notification to the user, wherein the outputting the notification to the user comprises generating information for notifying the user that the second region has a blur, when the user performs three-dimensional observation.

2. The image processing apparatus according to claim 1, wherein the processing circuitry is configured to set, as the third region, at least one of:

a region where the motion information of the treatment instrument is larger than a predetermined value; and a region of a distal end of the treatment instrument computed using at least one of the position information and the shape information.

3. The image processing apparatus according to claim 1, wherein the processing circuitry is configured to:

detect, by using first color information, a fourth region in one of the left image and the right image that indicates the treatment instrument used by the user;

set a fifth region by using second color information, the fifth region being a living-body region around the fourth region; and set at least one of the third region and the fifth region as the second region.

4. The image processing apparatus according to claim 3, wherein the processing circuitry is configured to set, as the fifth region, a region having a color feature close to a color of a living body and adjacent to the fourth region by using at least one of color saturation and hue.

5. The image processing apparatus according to claim 1, wherein the processing circuitry is configured to calculate a degree of interest for each of regions where the user is performing treatment, and to set a region having a high degree of interest as the second region.

6. The image processing apparatus according to claim 5, wherein the processing circuitry is configured to calculate the degree of interest for each region in the left image and the right image based on at least one of:

a distance from a center position of each of the left image and right image;

the motion information of the treatment instrument; and information related to a degree of being at a distal end of the treatment instrument obtained from at least one of the position information and the shape information of the treatment instrument.

7. An endoscope system, comprising:
the image processing apparatus according to claim 1; and
the endoscope.

8. An image processing apparatus for an endoscope, the apparatus comprising processing circuitry configured to:

acquire a pair of a left image and right image;

generate a three-dimensional display image for three-dimensional observation by a user based on the pair of the left image and right image;

set a first region in a part of one of the left image and the right image, the first region being a region having a blur;

set a second region in one of the left image and the right image, the second region being a region where the user is performing treatment;

compute an overlapping region between the first region and the second region;

determine whether or not to notify the user based on at least one of (i) a size of the overlapping region, (ii) a degree of interest of the overlapping region, and (iii) a contrast difference between the overlapping region and a region corresponding to the overlapping region in a remaining image of the left image and right image; and generate information for notifying the user that the second region has a blur, when the user is to be notified and the user performs three-dimensional observation.

9. The image processing apparatus according to claim 8, wherein the processing circuitry is configured to calculate the degree of interest for each region in the left image and the right image based on at least one of:

a distance from a center position of each of the left image and right image;

motion information of a treatment instrument; and information related to a degree of proximity to a distal end of the treatment instrument obtained from at least one of position information on an image of the treatment instrument and shape information of the treatment instrument.

10. The image processing apparatus according to claim 6, wherein the processing circuitry is configured to calculate the degree of interest for each region in the left image and the right image such that the degree of interest decreases as the distance from the center position to the region increases.

11. The image processing apparatus according to claim 6, wherein the processing circuitry is configured to calculate the degree of interest for each region in the left image and right image such that the degree of interest increases as an amount of motion of the treatment instrument in the region increases.

12. The image processing apparatus according to claim 6, wherein the processing circuitry is configured to calculate the degree of interest for each region in the left image and right image such that the degree of interest increases as the degree of being at the distal end of the treatment instrument to the region increases.

13. An image processing apparatus for an endoscope, the apparatus comprising processing circuitry configured to:

acquire a pair of a left image and right image;

generate a three-dimensional display image for three-dimensional observation by a user based on the pair of the left image and right image;

set a first region in a part of one of the left image and the right image, the first region being a region having a blur;

set a second region in a part of each of the left image and the right image by (i) calculating a degree of interest for each region in the left image and the right image in which the user is performing treatment, based on a distance from a center position of each of the left image and the right image, and (ii) setting, as the second region, a region calculated as having a high degree of interest;

determine whether or not the first region at least partially overlaps with the second region;

in response to determining that the first region at least partially overlaps with the second region, outputting a notification to the user; and in response to determining that the first region does not at least partially overlap with the second region, not outputting the notification to the user, wherein the outputting the notification to the user comprises generating information for notifying the user that the second region has a blur, when the user performs three-dimensional observation.

14. The image processing apparatus according to claim 13, wherein the processing circuitry is configured to calculate the degree of interest for each region in the left image and the right image such that the degree of interest decreases as the distance from the center position to the region increases.

* * * * *